(12) United States Patent
Cotticelli et al.

(10) Patent No.: US 7,470,526 B2
(45) Date of Patent: Dec. 30, 2008

(54) CHEMO-ENZYMATIC PROCESS FOR THE PREPARATION OF ESCITALOPRAM

(75) Inventors: Giovanni Cotticelli, Milan (IT); Silvia Rocchietti, Domodossola (IT); Marco Terreni, Milan (IT); Massimo Pregnolato, Carbonara al Ticino (IT); Raul Salvetti, Malonno (IT)

(73) Assignee: Adorken Technology SpA, S. Costa Volpino (Bergamo) (IT)

( * ) Notice: Subject to any disclaimer, the term of this patent is extended or adjusted under 35 U.S.C. 154(b) by 0 days.

(21) Appl. No.: 11/544,205

(22) Filed: Oct. 6, 2006

(65) Prior Publication Data

US 2007/0238887 A1    Oct. 11, 2007

Related U.S. Application Data

(63) Continuation-in-part of application No. PCT/IB2005/001067, filed on Apr. 7, 2005.

(30) Foreign Application Priority Data

Apr. 9, 2004    (IT)    ............ MI2004A0717

(51) Int. Cl.
 *C12P 17/04*    (2006.01)
(52) U.S. Cl. .............. 435/126; 435/128; 549/467
(58) Field of Classification Search ............ 549/467; 435/127, 128
See application file for complete search history.

(56) References Cited

U.S. PATENT DOCUMENTS

| 4,136,193 A | 1/1979 | Bogeso et al. |
| 4,650,884 A | 3/1987 | Bogeso |
| 6,365,747 B1 | 4/2002 | Dall'Asta et al. |
| 2003/0060641 A1 | 3/2003 | Petersen et al. |

FOREIGN PATENT DOCUMENTS

| EP | 0 171 943 B1 | 11/1988 |
| EP | 0 501 310 A | 9/1992 |
| EP | 0 347 066 B1 | 3/1995 |
| WO | WO 03/000672 A1 | 1/2003 |
| WO | WO 03/006449 A1 | 1/2003 |
| WO | WO 03/051861 A1 | 6/2003 |
| WO | WO 2004/014821 A1 | 2/2004 |

OTHER PUBLICATIONS

Solares et al., *Tetrahedron Assymetry*, 15(2):341-345 (2004).

*Primary Examiner*—B. Dentz
*Assistant Examiner*—David E Gallis
(74) *Attorney, Agent, or Firm*—Perkins Coie LLP

(57) ABSTRACT

A process for preparing an intermediate for synthesizing escitalopram and the pharmaceutically acceptable salts thereof from 4-(4-dimethylamino)-1-(4'-fluorophenyl)-1-(hydroxybutyl)-3-(acyloxymethyl)benzonitrile is described. The process involves converting said intermediate into the (S+) enantiomer of citalopram by means of enzymatic enantiomeric resolution.

18 Claims, 1 Drawing Sheet

CHEMO-ENZYMATIC PROCESS FOR THE PREPARATION OF ESCITALOPRAM

CROSS-REFERENCE TO RELATED APPLICATIONS

This application is a continuation-in-part of PCT Application No. PCT/IB2005/001067, filed Apr. 7, 2005, which claims the benefit of Italian Application No. MI2004A000717, filed Apr. 9, 2004, both incorporated herein by reference in their entirety.

TECHNICAL FIELD

The present invention relates to a process for preparing enantiomerically pure 1-(3-dimethylaminopropyl)-1-(4'-fluorophenyl)-1,3-dihydroisobenzofuran-5-carbonitrile.

BACKGROUND

The above-mentioned compound, whose structural formula is set forth below,

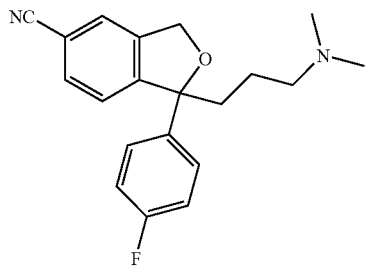

is a known active ingredient, also known as "citalopram", which is used for preparing pharmaceutical compositions intended for the treatment of depression.

Citalopram was described for the first time in Belgian patent application BE850401 (and in corresponding U.S. Pat. No. 4,136,193). A number of patent documents further relate to methods for its preparation.

With a chiral center, citalopram is generally produced and marketed in the form of a racemic mixture. As set forth in EP347066, the S(+) enantiomer, better known as escitalopram, is responsible for essentially the entire pharmacological activity of racemic citalopram. European patent application EP347066 describes two methods for preparing escitalopram.

The first method begins with racemic 4-(4-dimethylamino)-1-(4'-fluorophenyl)-1-(hydroxybutyl)-3-(hydroxymethyl)benzonitrile, which is subsequently esterified with an enantiomerically active acyl chloride, such as (+) or (−)-α-methoxy-α-trifluoromethylphenylacetyl chloride. From each (+) and (−) acyl chloride, two diastereoisomeric esters, which are separated by means of high performance liquid chromatography ("HPLC"), are obtained. The resulting enantiomerically pure ester, and subsequent cyclization in the presence of potassium t-butoxide in toluene, allows for the isolation of the pure enantiomer of citalopram from each ester.

The second method begins with enantiomerically pure 4-(4-dimethylamino)-1-(4'-fluorophenyl)-1-(hydroxybutyl)-3-(hydroxymethyl)benzonitrile (for example, (+)). In order to obtain this enantiomerically pure product, the amine is salified with an enantiomerically active acid, such as, for example, tartaric acid, in order to provide two diastereoisomeric salts which can be separated by crystallization. The pure enantiomer which is released from its salt is esterified to form a particularly labile ester (for example, with methane sulphonyl chloride) which, with the use of strong organic bases (for example, triethylamine), allows enantiomerically pure citalopram to be obtained.

Other methods for preparing escitalopram are described, for example, in U.S. Pat. No. 6,365,747, in U.S. patent application Ser No. US2003/0060641, and in international patent applications WO03/000672, WO03/006449 and WO03/051861.

The above-described methods are, however, characterized by the use of enantiomerically active acids and/or diastereoisomeric separations by crystallization or by means of HPLC, which set limits in terms of scalability of the process and reaction yields.

BRIEF SUMMARY

The recited aspects and embodiments of the claimed invention described and illustrated below are meant to be exemplary and illustrative, not limiting in scope.

Applicants have found a new process which allows for the preparation of escitalopram with a high level of enantiomeric purity without the disadvantages of the above-mentioned processes. In one aspect, a process for preparing an intermediate for synthesizing escitalopram and the pharmaceutically acceptable salts thereof from 4-(4-dimethylamino)-1-(4'-fluorophenyl)-1-(hydroxybutyl)-3-(acyloxymethyl)benzonitrile is described. The process involves converting said intermediate into the S(+) enantiomer of citalopram by means of enzymatic enantiomeric resolution.

In addition to the exemplary aspects and embodiments described above, further aspects and embodiments will become apparent by reference to the following description.

DETAILED DESCRIPTION

The Claimed Process

Figure 1:
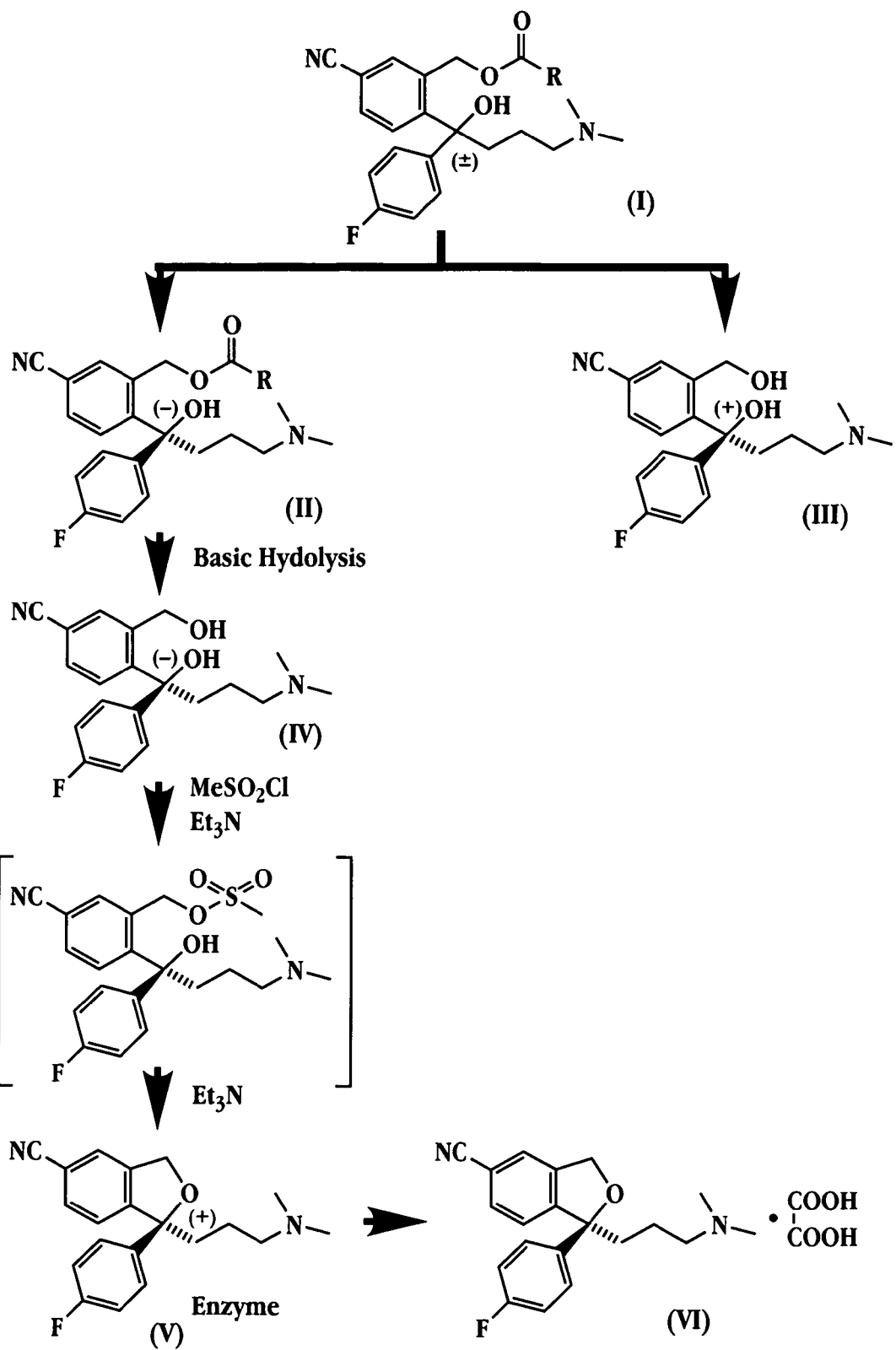
FIG. 1 sets forth a reaction diagram, which displays both the resolution and the conversion of the intermediate into escitalopram.

The process according to the present invention comprises enzymatic resolution by means of an esterase from *Aspergillus niger* of the racemic mixture of a compound having formula I,

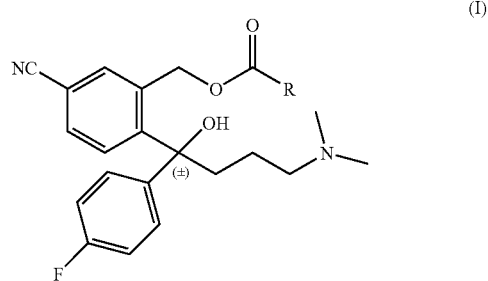

where R represents a $C_1$-$C_4$ alkyl radical or an aryl radical in order to provide the corresponding (−) enantiomer having formula II.

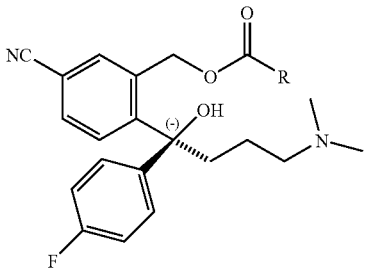

(II)

In fact, it has surprisingly been found, and constitutes the main subject-matter of the present invention, that, unlike the esterases generally known in the art, esterases from *Aspergillus niger* are able to selectively hydrolyze solely the (+) enantiomer of the racemic mixture (I), thereby allowing the (−) enantiomer to be collected at high levels of yield and optical purity.

The (−) enantiomer obtained in this manner can therefore be converted by means of hydrolysis, preferably basic hydrolysis, into (−)4-(4-dimethylamino)-1-(4'-fluorophenyl)-1-(hydroxybutyl)-3-(hydroxymethyl)-benzonitrile having formula IV.

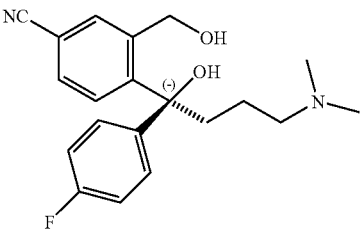

(IV)

This can then be converted into escitalopram having formula V,

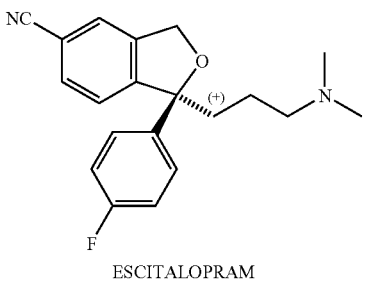

(V)

ESCITALOPRAM by means of condensation of the two hydroxyl groups using methods known in the art, such as, for example, the method described in EP347066 (that is, processing with $CH_3SO_2Cl$ in the presence of $Et_3N$), which is incorporated herein by reference.

The reaction diagram, comprising both the resolution and the conversion into escitalopram, is set forth in FIG. 1.

The racemic mixture of the compound having formula (I) can in turn be prepared according to methods known in the art. For example, it can be prepared by following the instructions set forth in EP171943, incorporated herein by reference in its entirety. EP-171943 describes a synthesis method which provides for two consecutive Grignard reactions beginning with 5-cyanophthalide; the first with 4-fluorophenylmagnesium bromide and the second with 3-(dimethylamino)propylmagnesium chloride on the magnesium derivative obtained in this manner in order to obtain a magnesium intermediate which, following acid hydrolysis, brings the precursor of citalopram to the diol having formula I'.

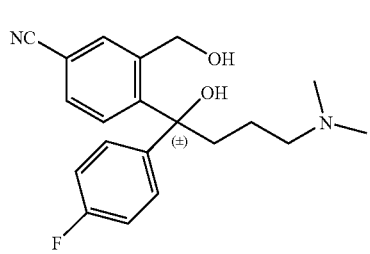

(I')

This intermediate is then acylated selectively on the hydroxymethyl in position 3 (of the benzonitrile) according to methods known in the art, for example, by reaction with the anhydride or the chloride of the corresponding acid.

According to a preferred embodiment, 4-(4-dimethylamino)-1-(4'-fluorophenyl)-1-(hydroxybutyl)-3-(hydroxymethyl)-benzonitrile is acetylated on the hydroxymethyl residue by using acetyl chloride. In this reaction, 5-20 moles of acetyl chloride are used, preferably approximately 17 moles, per mole of starting product. The starting product is preferably added to the reaction medium while maintaining a preferred temperature of between 30 and 35° C. Once the addition operations have been carried to completion, the 4-(4-dimethylamino)-1-(4'-fluorophenyl)-1-(hydroxybutyl)-3-(acyloxymethyl)benzonitrile compound is readily isolated according to methods known in the art, for example, by evaporation at reduced pressure.

The resolution step is carried out in a solvent comprising a mixture of an alcohol (preferably a $C_1$-$C_4$ alcohol, and even more preferably MeOH) and water, preferably in a proportion of from 0.5-1.5 to 1, even more preferably in a proportion of 1 to 1, effected at a preferred temperature of from 15-35° C., preferably between 20 and 25° C.

Water is used in the form of a phosphate buffer, preferably a monobasic potassium phosphate buffer.

The solvent is advantageously used at a quantity of from 3-5 liters, preferably from 3.5-4 liters, per mole of substrate.

In a preferred embodiment, the racemic compound having formula I is initially added to the solvent at a basic pH value, preferably approximately 8, and is subsequently brought to a value of 6.

The esterase enzyme from *Aspergillus niger*, preferably immobilized on resin, generally epoxy resin (Eupergit C), is then added and is advantageously used at a quantity of from 2500-3200 units, preferably from 2800-2900 units, per mole of substrate.

The resolution reaction is monitored by means of HPLC and allowed to continue until a hydrolysis yield of 55% is reached. Such a yield is normally reached after approximately 70-80 hours. After filtration, extraction is carried out using ethyl acetate as the preferred solvent and, after subsequent evaporation and suitable crystallization using a mixture of diethyl ether/ethyl acetate, solely (−)4-(4-dimethylamino)-1-(4'-fluorophenyl)-1-(hydroxybutyl)-3-(acyloxymethyl)benzonitrile is obtained.

Starting from this intermediate with reference to patent EP347066, it is possible, after hydrolysis and subsequent termination of the cycle, to obtain solely the escitalopram, obtained as a free base (V) or in the form of an oxalate salt (VI).

For the purposes of the present invention, the terms "racemic mixture", "racemate" and "racemic compound" are intended to refer not only to a 50:50 mixture of the two individual enantiomers, but also to a mixture in which one of the two enantiomers is present in excess with respect to the remaining enantiomer.

The examples below are intended purely by way of illustration and are not considered to limit the invention.

EXAMPLES

Example 1

Synthesis of 4-(4-dimethylamino)-1-(4'-fluorophenyl)-1-(hydroxybutyl)-3-(acetoxymethyl)benzonitrile 58.7 g of 4-(4-dimethylamino)-1-(4'-fluorophenyl)-1-(hydroxybutyl)-3-(hydroxymethyl)benzonitrile were placed in a 4-neck flask in a water bath at between 30 and 35° C., preferably 35° C., and 210 ml of acetyl chloride (17 moles per mole of starting product) were added dropwise into this medium. The admixture was left under agitation for 5 minutes, transferred to a 1-neck flask and evaporated at reduced pressure. 79.02 g of 4-(4-dimethylamino)-1-(4'-fluorophenyl)-1-(hydroxybutyl)-3-(acetoxymethyl)benzonitrile in the form of an orange oily residue was obtained. $^1$H NMR (DMSO-d6) δ 7.9 (d, 1H ), 7.8 (d, 1H), 7.75 (s, 1H), 7.2 (d, 2H), 7.1 (d, 2H), 6.2 (s, 1H), 5.2 ( d, 1H), 4.8 (d, 1H), 3.0 (m, 2H), 2.60 (m, 6H), 2.3 (s, 2H), 1.9 ( s, 3H), 1.7 (m, 1H), 1.4 ( m, 1H).

Example 2

Enzymatic Resolution of 4-(4-dimethylamino)-1-(4'-fluorophenyl)-1-(hydroxybutyl)-3-(acetoxymethyl) benzonitrile 10 g of 4-(4-dimethylamino)-1-(4'-fluorophenyl)-1-(hydroxybutyl)-3-(acetoxymethyl)benzonitrile (250 mM) were dissolved in 52 ml of MeOH, to which 52 ml of a 25 mM, pH8 monobasic potassium phosphate buffer were subsequently added.

The pH was then brought to 6 by carrying out suitable modifications with 2N HCl and compensating for the volume of HCl added with the same amount in ml of MeOH in order not to change the composition of the solution. The temperature of the solution was controlled so as to be in the range of between 20 and 25° C.

Finally, approximately 75 units of esterase enzyme derivative was added to the solution. The esterase enzyme derivative was obtained from crude lipase extract from *Aspergillus niger* and immobilized on epoxy resin, such as Eupergit C, according to conventional processes.

The reaction was carried out using an automatic titrator so as to keep the pH constant and was monitored by means of HPLC until a hydrolysis level of 55% (from 70-80 hours) was obtained, with which 99% e.e. was obtained.

At the end of the reaction, the enzyme was filtered and washed with a minimum quantity of H$_2$O-MeOH solution (from 5-10 ml).

The reaction solution was evaporated at reduced pressure and the aqueous phase, suitably basified to pH 8.5, was extracted with ethyl acetate (approximately 70 ml, 4 times) in the presence of NaCl (approximately 5 g).

The extraction was monitored by means of HPLC according to the following analysis conditions with a Shimadzu HPLC column: chiral AGP 10 cm×4×5 Φ

Eluent: 2% CH$_3$CN, V 98% potassium phosphate buffer at 10 mM pH=4.67

Flow: 0.9 ml/min, UV/visible detection (λ=237 nm)

The organic phase containing 4-(4-dimethylamino)-1-(4'-fluorophenyl)-1-(hydroxybutyl)-3-(acyloxymethyl)benzonitrile and part of the diol were evaporated at reduced pressure. The crude reaction product (8 g) is thus obtained and then had to be purified by crystallization.

Example 3

Synthesis of (−)4-(4-dimethylamino)-1-(4'-fluorophenyl)-1-(hydroxybutyl)-3-(hydroxymethyl)benzonitrile The crude product isolated by the preceding reaction (8 g) was dissolved with diethyl ether (approximately 40 ml). A minimum quantity of ethyl acetate (0.1 ml) was added and the mixture was heated gently. Precipitation of a solid was obtained by cooling. The filtrate was subjected to a second crystallization operation and, after cooling to from 0-4° C., precipitation of solely (−)4-(4-dimethylamino)-1-(4'-fluorophenyl)-1-(hydroxybutyl)-3-(acetoxymethyl)-benzonitrile as a white solid (2.2 g) with a purity of 98% and with 99.8% e.e., $[α]_D$=−39.87/−40.00 was obtained. The solid obtained was subsequently dissolved in 175 ml of 30% NH$_3$ and in 100 ml of MeOH, the solution was left under agitation for approximately 4 hours and subsequently evaporated to produce 1.9 g of (−)4-(4-dimethylamino)-1-(4'-fluorophenyl)-1-(hydroxybutyl)-3-(hydroxymethyl)benzonitrile.

Example 4

Enzymatic Screening for the Racemic Resolution of Citalopram Intermediates

A. Hydrolysis of Citalopram Intermediate Using Lipases

Applicants studied the hydrolysis of citalopram intermediate by using immobilized lipases (see scheme 1) isolated from different microbial sources.

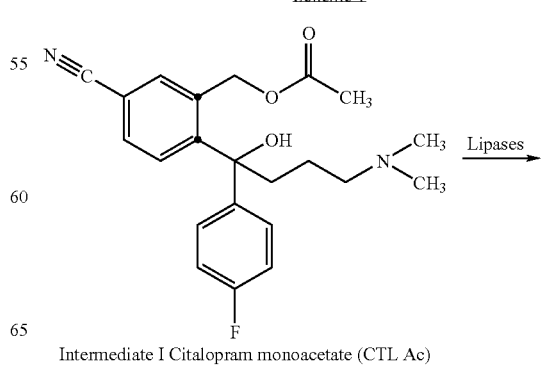

Scheme 1

Intermediate I Citalopram monoacetate (CTL Ac)

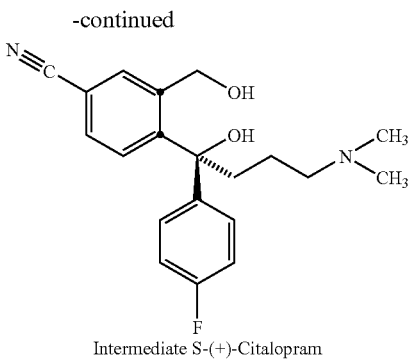

Intermediate S-(+)-Citalopram

The hydrolysis reaction was carried out under standard conditions (pH 8 and 25° C.), in phosphate buffer (NaH2PO4 25 mM). As reported below, these reactions do not show a high enantioselective efficiency as shown by the enantiomeric excess ("e.e.") and E values reported in table 1.

TABLE 1

| Enzymatic derivative | % conversion (time) | % e.e. (S) | E (S) |
| --- | --- | --- | --- |
| IB-CRL A0 | 8.9 (48 h) | 3.4 | n.d. |
| IB-PSL A0 | 15.0 (48 h) | 12.5 | n.d. |
| IB-PFL A0 | 10.2 (48 h) | 1.8 | n.d. |
| IB-PPL A0 | 9.1 (48 h) | 2.6 | n.d. |
| IB-ANL A0 | 15.4 (66 h) | 1.7 | n.d. |

Reaction Conditions: Volume: 10 mL; Concentration: 10 mM in buffer NaH2PO4 25 mM; pH 8; T = 25° C.

B. Hydrolysis of Citalopram Intermediate Using Esterases

In a second approach, the racemic resolution was studied by employing esterases as the immobilized enzyme, using the same reaction conditions described above. As reported below, these enzymes display a good kinetic profile (Table 2).

TABLE 2

| Enzymatic derivative | % conversion | % e.e. (S) | E (S) |
| --- | --- | --- | --- |
| IB-PLE E1 G | 50.3 | 14.0 | 1.5 |
| IB-PPLE E1 G | 19.5 | 5.3 | — |
| IB-AA E1 | 54.0 | 20.0 | 1.7 |
| IB-CLE E1 | — | — | — |
| IB-CE E1 | — | — | — |
| IB-ANL-LAZE-A0 E1 | 51.5 | 57.0 | 5.7 |

Conditions: Final Volume: 10 mL; Concentration: 10 mM in phosphate buffer 25 mM; pH 8; T = 25° C.

In particular, IB-ANL-LAZE-A0 E1 (obtained by immobilizing *aspergillus niger* esterase) shows a good e.e. (57) value under these reaction conditions.

C. Studies and Optimisation of Racemic Resolution of Citalopram Intermediate by Using IB-ANL-LAZE-A0 E1

The hydrolysis reaction was studied under different testing conditions whereby the pH and temperature were varied (Table 3) by using IB-ANL-LAZE-A0 E1 G as the immobilized enzyme. As reported in the table, the optimal hydrolysis conditions are pH 6 and 25° C.

TABLE 3

| pH | T | % conversion (time) | % e.e. (S) | E (S) |
| --- | --- | --- | --- | --- |
| 8 | 25 | 50.6 (3 h) | 61.0 | 7.0 |
| 6 | 25 | 51.3 (3 h) | 65.0 | 8.1 |
| 6 | 4 | 50.3 (6 h) | 66.0 | 9.2 |
| 5 | 4 | 50.3 (8 h) | 66.0 | 9.2 |

Testing Conditions volume: 10 mL; Concentration: 10 mM in phosphate buffer 25 mM; enzymatic derivative: IB-ANL-LAZE-A0 E1 G.

Further, the study was carried out by using different solvents and analyzing the effects of different solventconcentrations in the reaction medium. The solvents that show the better e.e. values are the alcoholic solvents (EtOH, MeOH).

In conclusion, the conversion yield and the enantiomeric excess achieved by resolving the racemic mixture of citalopram with a lipase are very poor (Table 1). When the lipase is replaced with an esterase, both the conversion yield and the enantiomeric excess increase (Table 2). In particular, by using an esterase from *Aspergillus niger* (i.e., ANL), an enantiomeric excess is obtained which is at least 185% higher than that which may be achieved with other known esterases.

By optimizing the reaction conditions and by choosing a good enzymatic derivative, Applicants obtained a good enatioselectivity in the racemic resolution of Citalopram intermediate.

Materials and Methods

HPLC Instrumentation:

Equipment:

HPLC. Merck-Hitachi

Detector: Spectrophotometer UV-Visible

Column: Zorbax SB C18, 5 μm, 4.6×250 mm

Eluent Mixture:

| 60% Phosphate Buffer KH$_2$PO$_4$ 10 mM - 40% Acetonitrile | pH = 4.00 |
| --- | --- |

Cromatograpic Conditions:

Injection Volume: 10 uL

Injected Concentration: 0.25 mM

Flow: 1 mL/min

Detector UV: 237 nm

Temperature: 25° C.

Retention Times:

| Citalopram Intermediate I | $T_R$ = 3.21 |
| --- | --- |
| Monoacetilate at primary OH Citalopram Intermediate I | $T_R$ = 4.62 |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A process for preparing escitalopram, said process comprising the resolution by means of an esterase from *Aspergillus niger* of a racemic mixture of a compound having formula I

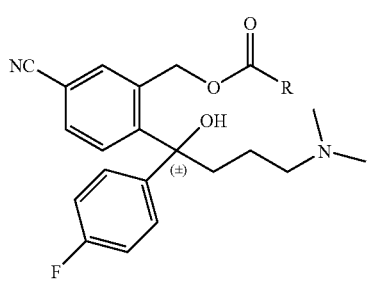
(I)

wherein R represents a $C_1$-$C_4$ alkyl radical, in order to provide the corresponding (−) enantiomer having formula II

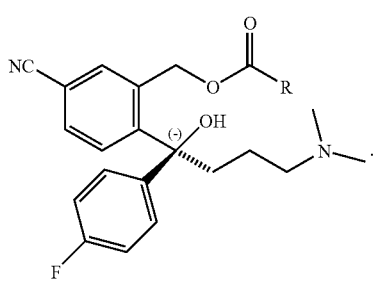
(II)

2. A process according to claim 1, wherein the resolution is carried out in a solvent constituted by a mixture of an alcohol and water.

3. A process according to claim 2, wherein the alcohol is a $C_1$-$C_4$ alcohol.

4. A process according to claim 2, wherein the alcohol is MeOH.

5. A process according to claim 2, wherein the alcohol and water are present in a proportion of from 0.5-1.5 to 1 by volume.

6. A process according to claim 2, wherein the alcohol and water are present in a proportion of 1 to 1 by volume.

7. A process according to claim 2, wherein the water is used in the form of a phosphate buffer.

8. A process according to claim 2, wherein the water is used in the form of a monobasic potassium phosphate buffer.

9. A process according to claim 1, wherein the resolution is carried out at a temperature of from 15-35° C.

10. A process according to claim 1, wherein the resolution is carried out at a temperature of between 20 and 25° C.

11. A process according to claim 1, wherein the solvent is used at a quantity of from 3-5 liters, per mole of compound having formula I.

12. A process according to claim 1, wherein the solvent is used at a quantity of from 3.5-4 liters, per mole of compound having formula I.

13. A process according to claim 1, wherein the esterase from *Aspergillus niger* is immobilized on resin.

14. A process according to claim 1, wherein the esterase from *Aspergillus niger* is immobilized on epoxy resin.

15. A process according to claim 1, wherein the esterase from *Aspergillus niger* is used in a quantity of from 2500-3200 units, per mole of compound having formula I.

16. A process according to claim 1, wherein the esterase from *Aspergillus niger* is used in a quantity of from 2800-2900 units, per mole of compound having formula I.

17. A process according to claim 1, wherein the (−) enantiomer having formula II is converted by means of hydrolysis into benzonitrile having formula IV,

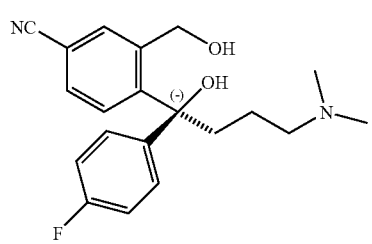
(IV)

which is subsequently converted into escitalopram by means of condensation of the two hydroxyl groups.

18. A process according to claim 1, wherein the compound having formula I is obtained by acylation of a compound having formula I'

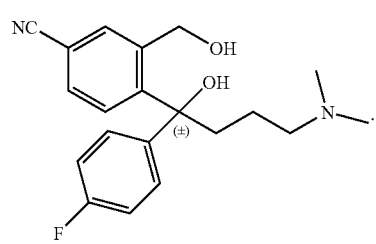
(I')

* * * * *